United States Patent
Hu et al.

(10) Patent No.: US 10,973,434 B2
(45) Date of Patent: Apr. 13, 2021

(54) SYSTEM AND METHOD FOR PHASE-CONTRAST MRI WITH HYBRID ONE-AND TWO-SIDED FLOW ENCODING AND VELOCITY SPECTRUM SEPARATION (HOTSPA)

(71) Applicant: The Regents of the University of California, Oakland, CA (US)

(72) Inventors: Peng Hu, Los Angeles, CA (US); Da Wang, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 398 days.

(21) Appl. No.: 16/080,644

(22) PCT Filed: Feb. 28, 2017

(86) PCT No.: PCT/US2017/019814
§ 371 (c)(1),
(2) Date: Aug. 28, 2018

(87) PCT Pub. No.: WO2017/151536
PCT Pub. Date: Sep. 8, 2017

(65) Prior Publication Data
US 2019/0053735 A1   Feb. 21, 2019

Related U.S. Application Data

(60) Provisional application No. 62/301,395, filed on Feb. 29, 2016.

(51) Int. Cl.
*A61B 5/055*  (2006.01)
*G01R 33/563*  (2006.01)

(52) U.S. Cl.
CPC .......... *A61B 5/055* (2013.01); *G01R 33/5635* (2013.01); *G01R 33/56316* (2013.01);
(Continued)

(58) Field of Classification Search
CPC ............. A61B 5/055; G01R 33/56325; G01R 33/56316; G01R 33/5635; G01R 33/56308; G01R 33/56333; G06T 2207/10088
See application file for complete search history.

(56) References Cited

U.S. PATENT DOCUMENTS 5,828,215 A   10/1998  Boettcher
2008/0054900 A1   3/2008  Polzin
(Continued)

OTHER PUBLICATIONS

Bernstein MA, et al. Reconstructions of phase contrast, phased array multicoil data. Magn. Reson. Med. 1994;32:330-334. doi: 10.1002/mrm.1910320308.
(Continued)

*Primary Examiner* — Luther Behringer
*Assistant Examiner* — Adil Partap S Virk
(74) *Attorney, Agent, or Firm* — Quarles & Brady LLP

(57) ABSTRACT

A system and method is provided for acquiring flow encoded data from a subject using a magnetic resonance imaging (MRI) system. The method includes acquiring flow encoded (FE) data with alternating encoding polarities and along two of three orthogonal directions through the subject over at least two cycles of the flow within the subject; and separating the FE data into directional FE datasets using a temporal filter that separates the FE data based on temporal modulation of the FE directions caused by the alternating encoding polarities extending over the at least two cycles of the flow within the subject that shift the Fourier spectrum of velocity waveforms corresponding to the FE data. The method also includes using the directional FE datasets to generate an image of the subject showing flow within the subject caused by the at least two cycles of flow within the subject.

7 Claims, 11 Drawing Sheets

(52) U.S. Cl.
CPC ............. *G01R 33/56325* (2013.01); *G06T 2207/10088* (2013.01)

(56) References Cited

U.S. PATENT DOCUMENTS

| | | | |
|---|---|---|---|
| 2009/0256568 | A1 | 10/2009 | Wiesenger |
| 2010/0085052 | A1 | 4/2010 | Johnson |
| 2011/0064294 | A1 | 3/2011 | Abe |
| 2015/0338490 | A1 | 11/2015 | Greiser |

OTHER PUBLICATIONS

Bock J, et al. In vivo noninvasive 4D pressure difference mapping in the human aorta: Phantom comparison and application in healthy volunteers and patients. Magn. Reson. Med. 2011;66:1079-1088. doi: 10.1002/mrm.22907.

Breuer FA, et al. Controlled aliasing in parallel imaging results in higher acceleration (CAIPIRINHA) for multi-slice imaging. Magn Reson Med 2005;53:684-691.

Callaghan FM, et al. Use of multi-velocity encoding 4D flow MRI to improve quantification of flow patterns in the aorta. J. Magn. Reson. Imaging 2015:n/a-n/a. doi: 10.1002/jmri.24991.

Conturo TE, et al. Analysis of encoding efficiency in MR imaging of velocity magnitude and direction. Magn Reson Med 1992;25:233-247.

Griswold MA, et al. Generalized autocalibrating partially parallel acquisitions (GRAPPA). Magn Reson Med 2002;47:1202-1210.

Gu T, et al. PC VIPR: a high-speed 3D phasecontrast method for flow quantification and high-resolution angiography. Am J Neuroradiol 2005;26:743-749.

Hansen MS, et al. Accelerated dynamic Fourier velocity encoding by exploiting velocity-spatio-temporal correlations. Magn Reson Mater Phys Biol Med 2004;17:86-94.

Huang F, et al. k-t GRAPPA: a k-space implementation for dynamic MRI with high reduction factor. Magn Reson Med 2005;54:1172-1184.

International Search Report & Written Opinion for PCT/US2017/019814, dated May 31, 2017, 11 pages.

Jung B, et al. Highly k-t-space—accelerated phase-contrast MRI. Magn Reson Med 2008;60:1169-1177.

Jung B, et al. Investigating myocardial motion by MRI using tissue phase mapping. Eur J Cardiothorac Surg 2006;29: S150-S157.

Kim D, et al. Accelerated phase-contrast cine MRI using k-t Sparse-Sense. Magn Reson Med 2012;67:1054-1064.

Kwak Y, et al. Accelerated aortic flow assessment with compressed sensing with and without use of the sparsity of the complex difference image. Magn Reson Med 2013;70:851-858.

Lin H-Y, et al. Shared velocity encoding: A method to improve the temporal resolution of phase-contrast velocity measurements. Magn. Reson. Med. 2012;68:703-7100 doi: 10.1002/mrm.23273.

Lustig M, et al. Sparse MRI: the application of compressed sensing for rapid MR imaging. Magn Reson Med 2007;58:1182-1195.

Madore B, et al. Unaliasing by Fourier-encoding the overlaps using the temporal dimension (UNFOLD), applied to cardiac imaging and fMRI. Magn Reson Med 1999;42:813-828.

Markl M, et al. 4D-flow MRI. J Magn Reson Imaging 2012;36:1015-1036.

Markl M, et al. Myocardial T2-mapping and velocity mapping: changes in regional left ventricular structure and function after heart transplantation. Magn Reson Med 2013;70:517-526.

Middione MJ, et al. Convex gradient optimization for increased spatiotemporal resolution and improved accuracy in phase contrast MRI. Magn Reson Med 2014;72:1552-1564.

Negahdar M, et al. Comparison of Cartesian, UTE radial, and spiral phase-contrast MRI in measurement of blood flow in extracranial carotid arteries: normal subjects. SPIE Proc 2013;8672:86720A-86720A-9.

Pelc, NJ, et al. Phase contrast cine magnetic resonance imaging. Magn. Reson. Q. 1991;7:229-254.

Pruessmann KP, et al. Sense: sensitivity encoding for fast MRI. Magn Reson Med 1999;42:952-962.

Santini F, et al. The More the Merrier? Finding the "Right" Temporal Resolution for Blood Velocity Measurements: a Multimodal Study, In: Proceedings of 15th Annual Meeting of ISMRM, Toronto, Canada, 2015. Abstract 2741.

Srichai MB, et al. Cardiovascular applications of phase-contrast MRI. Am J Roentgenol 2009;192:662-675.

Tao Y, et al. Carotid blood flow measurement accelerated by compressed sensing: validation in healthy volunteers. Magn Reson Imaging 2013;31:1485-1491.

Thompson RB, et al. High temporal resolution phase contrast MRI with multiecho acquisitions. Magn Reson Med 2002;47:499-512.

Vanninen RL, et al. Carotid artery stenosis: clinical efficacy of MR phase-contrast flow quantification as an adjunct to MR angiography. Radiology 1995;194: 459-467.

Wang D, et al. Phase contrast MRI with flow compensation view sharing. Magn Reson Med 2015;73:505-513.

Wu C, et al, Effects of Temporal Resolution and Velocity Encoding Strategies on Aortic Flow Measurement with Two-Dimensional Phase-Contrast MRI, In: Proceedings of 15th Annual Meeting of ISMRM, Toronto, Canada, 2015. Abstract 2744.

European Patent Office, Partial Supplementary European Search Report for application 17760564, dated Oct. 8, 2019.

Wang, Da, et al. "Phase-contrast MRI with hybrid one and two-sided flow-encoding and velocity spectrum separation." Magnetic resonance in medicine 78.1 (2017): 182-192.

Grant, DM et al. "Phase Contrast MRA, Passage" Encyclopedia of Nuclear Magnetic Resonance vol. 6. Jan. 1, 1996, pp. 3570-3584.

European Patent Office, Extended European Search Report for application 17760564.9, dated Jan. 17, 2020.

FC/3FE (1 cardiac phase)

SYSTEM AND METHOD FOR PHASE-CONTRAST MRI WITH HYBRID ONE-AND TWO-SIDED FLOW ENCODING AND VELOCITY SPECTRUM SEPARATION (HOTSPA)

CROSS-REFERENCE TO RELATED APPLICATIONS

This application represents the national stage entry of International Application PCT/US2017/019814, filed Feb. 28, 2017, which claims benefit of and priority to U.S. Provisional Patent Application 62/301,395, filed Feb. 29, 2016, which is incorporated herein by reference in its entirety for all purposes.

BACKGROUND OF THE INVENTION

When a substance such as human tissue is subjected to a uniform magnetic field (polarizing field $B_0$), the individual magnetic moments of the nuclear spins in the tissue attempt to align with this polarizing field, but precess about it in random order at their characteristic Larmor frequency. Usually the nuclear spins are comprised of hydrogen atoms, but other NMR active nuclei are occasionally used. A net magnetic moment $M_z$ is produced in the direction of the polarizing field, but the randomly oriented magnetic components in the perpendicular, or transverse, plane (x-y plane) cancel one another. If, however, the substance, or tissue, is subjected to a magnetic field (excitation field $B_1$; also referred to as the radiofrequency (RF) field) which is in the x-y plane and which is near the Larmor frequency, the net aligned moment, $M_z$, may be rotated, or "tipped" into the x-y plane to produce a net transverse magnetic moment $M_t$, which is rotating, or spinning, in the x-y plane at the Larmor frequency. The practical value of this phenomenon resides in the signal which is emitted by the excited spins after the excitation field $B_1$ is terminated. There are a wide variety of measurement sequences in which this nuclear magnetic resonance (NMR) phenomenon is exploited.

When utilizing these signals to produce images, magnetic field gradients ($G_x$, $G_y$, and $G_z$) are employed. Typically, the region to be imaged experiences a sequence of measurement cycles in which these gradients vary according to the particular localization method being used. The emitted MR signals are detected using a receiver coil. The MRI signals are then digitized and processed to reconstruct the image using one of many well-known reconstruction techniques.

Magnetic resonance angiography (MRA) and, related imaging techniques, such as perfusion imaging, use the NMR phenomenon to produce images of the human vasculature or physiological performance related to the human vasculature. There are three main categories of techniques for achieving the desired contrast for the purpose of MR angiography. The first general category is typically referred to as contrast enhanced (CE) MRA. The second general category is phase contrast (PC) MRA. The third general category is time-of-flight (TOF) or tagging-based MRA.

To perform CE MRA, a contrast agent, such as gadolinium, is injected into the patient prior to the magnetic resonance (MR) angiogram to enhance the diagnostic capability of the MR angiogram. Perfusion imaging is employed to assess the viability of tissues. A contrast agent is administered to the subject and a series of MR images are acquired as the contrast agent perfuses into the tissues of interest. From this series of contrast-enhanced MR images hemodynamic parameters such as blood flow, blood volume, and mean transit time may be computed.

While CE MRA is a highly effective means for noninvasively evaluating the vascular and physiological performance, for example, by studying perfusion, the technique suffers from several additional drawbacks. First, the contrast agent that must be administered to enhance the blood vessel carries a significant financial cost. Second, contrast agents such as gadolinium have recently been shown to be causative of a debilitating and potentially fatal disorder called nephrogenic systemic fibrosis (NSF). Third, CE MRA, may not provide accurate or sufficient hemodynamic information, so that it is not always feasible to determine if a stenosis is hemodynamically significant or to assess the perfusion in a clinically useful manner.

As such, non-contrast enhanced (NE) MRA methods have become more prevalent. For example, TOF imaging techniques do not require the use of a contrast agent and do not rely on potentially-precarious velocity encoding sensitivities. Contrary to CE-MRA, which relies on the administered contrast agent to provide an increase in measured MR signal, TOF MRA relies on the inflow of blood into an imaging volume to increase the signal intensity of the vasculature as compared to the stationary background tissues. This is achieved by the application of a number of RF excitation pulses to the imaging volume that cause the magnetization of the stationary background tissues to reach a saturation value. Since inflowing blood entering the imaging volume is not exposed to the same number of RF excitation, it will provide higher MR signal intensity than the background tissue. The differences between the signal intensity of the stationary background tissues and the inflowing blood thus provide a contrast mechanism exploited by TOF MRA.

In an effort to increase contrast attributable to the relatively small signal levels or weight particular signals, for example, those attributable to cerebral blood flow (CBF) or another measurable mechanism, various "tagging" or "labeling" methods have been developed. One such method is referred to as the arterial spin labeling (ASL) family of techniques.

Phase contrast (PC) MRA techniques utilize the change in the phase shifts of the flowing protons in the region of interest to create an image. Spins that are moving along the direction of a magnetic field gradient receive a phase shift proportional to their velocity. Specifically, in a PC MRA pulse sequence, two data sets with a different amounts of flow sensitivity are acquired. This is usually accomplished by applying gradient pairs, which sequentially dephase and then rephase spins during the sequence. The first data set is acquired using a "flow-compensated" (FC) pulse sequence or a pulse sequence without sensitivity to flow. The second data set is acquired using a "flow-encoded" FE pulse sequence designed to be sensitive to flow. The amount of flow sensitivity is controlled by the strength of the bipolar gradient pairs used in the pulse sequence because stationary tissue undergoes no effective phase change after the application of the two gradients, whereas the different spatial localization of flowing blood is subjected to the variation of the bipolar gradient. Accordingly, moving spins experience a phase shift. The raw data from the two data sets are subtracted to yield images that illustrate the phase change, which is proportional to spatial velocity.

Although PC-MRI is typically performed with FE gradients applied in the slice direction in 2D acquisitions, the FE gradients can also be applied in more than one orientations, such as in 2D tissue phase mapping or 4D flow, to capture the blood flow/tissue motion in slice, phase-encoding, and frequency encoding directions. For these applications, the temporal resolution is typically poorer than conventional 2D PC-MRI due to the need to acquire the FC data and FE data in three directions for each cardiac phase. It has been shown that temporal resolution and temporal footprint of PC-MRI may affect the measurement accuracy of maximum peak velocity, which is an important index for diagnosis of a number of clinical diseases, such as carotid artery stenosis. Low temporal resolution and long temporal footprint can result in under-estimation of the maximum peak velocity as well as pressure gradients across valves or stenoses. Reducing views-per-segment, such that the number of k-space lines acquired for each cardiac phase within a single cardiac cycle is reduced, may improve temporal resolution. However, doing so it requires increased total image acquisition time.

Fast MRI techniques such as non-Cartesian sampling, parallel imaging, k-t space acceleration, and compressed sensing techniques have been developed to effectively reduce the total acquisition time of PC-MRI or to improve the temporal resolution. The temporal resolution may also be improved by several other techniques. A recently proposed shared velocity encoding (SVE) technique, as described in Lin H-Y, Bender J A, Ding Y, Chung Y-C, Hinton A M, Pennell M L, Whitehead K K, Raman S V, Simonetti O P. Shared velocity encoding: A method to improve the temporal resolution of phase-contrast velocity measurements. Magn. Reson. Med. 2012; 68:703-710. doi: 10.1002/mrm.23273, uses interleaved two-sided velocity encodings and sliding window subtractions, doubling the temporal resolution. However, the temporal footprint of each cardiac phase in the SVE technique is the same as traditional 2D PC-MRI, despite improved temporal resolution through view-sharing. Furthermore, the implementation of the SVE technique in three-dimensional PC-MRI implies even longer temporal footprint (=6*TR*views-per-segment) than conventional 4D flow acquisition (=4*TR*views-per-segment). The issue of temporal footprint is mitigated by the so-called FCVS technique, as described in Wang D, Shao J, Rapacchi S, Middione M J, Ennis D B, Hu P. Phase contrast MRI with flow compensation view sharing. Magn. Reson. Med. 2015; 73:505-513. doi: 10.1002/mrm.25133, where the FC data is under-sampled and view shared based on the assumption that the FC background phase data do not change as fast in time as the FE data.

Therefore, it would be desirable to have a system and method for providing the clinically-required information upon which clinicians have come to rely on PC MRI, but with improved temporal resolution and temporal footprint, particularly, within the context of 4D flow acquisitions.

SUMMARY

The present disclosure provides systems and methods for performing flow or velocity encoded magnetic resonance imaging (MRI) that overcomes the aforementioned drawbacks. More particularly, a phase contrast (PC-) MRI technique is provided that uses a hybrid one- and two-sided flow encoding and velocity spectrum separation, referred to herein as the HOTSPA technique. In the HOTSPA technique, the flow velocity encoding polarity is alternated, for example, between successive cardiac phases, for two flow-encoded (FE) directions and remains one-sided in the remaining FE direction. The flow-compensated (FC) data does not need to be explicitly acquired. For example, the HOTSPA technique allows separations of the Fourier velocity spectrum of the background phase (FC) waveform, as well as the velocity waveforms in the three FE directions, such as within the cardiac cycle. This enables 3D velocity calculation based on 2 samples in the 3D space of first-moment (M1) rather than 4 samples as in conventional 4D flow techniques. Compared to conventional PC-MRI, the HOTSPA technique can sample the hybrid M1-t space more efficiently and can reduce the temporal sampling period and temporal footprint of 4D flow acquisition by, for example, 50 percent.

In accordance with one aspect of the present disclosure, a method is provided for producing magnetic resonance angiographic (MRA) images of a subject. The method includes performing, using a magnetic resonance imaging (MRI) system, a phase-contrast pulse sequence to acquire imaging data by acquiring a first set of MR data that is flow encoded along a first direction ($FE_1$) using a two-sided flow-encoding strategy that is free of flow compensation and acquiring a second set of MR data that is flow encoded along a second direction ($FE_2$) and flow encoded along a third direction ($FE_3$) using a hybrid one- and two-sided flow encoding strategy. The method also includes separating the first set of MR data into a background phase signal $\phi_0(t)$ and a first directional phase signal $\phi_{v,1}(t)$ and separating the second set of MR data into a second directional phase signal $\phi_{v,2}(t)$ and a third directional phase signal $\phi_{v,3}(t)$. The method further includes reconstructing MRA images of the subject using the background phase signal $\phi_0(t)$, the first directional phase signal $\phi_{v,1}(t)$, the second directional phase signal $\phi_{v,2}(t)$, the third directional phase signal $\phi_{v,3}(t)$.

In accordance with another aspect of the present disclosure, a method is provided for acquiring flow encoded data from a subject using a magnetic resonance imaging (MRI) system to reconstruct an image of the subject illustrating flow within the subject. The method includes, using the MRI system, acquiring flow encoded (FE) data with alternating encoding polarities and along two of three orthogonal directions through the subject over at least two cycles of the flow within the subject. The method also includes separating the FE data into directional FE datasets using a temporal filter that separates the FE data based on temporal modulation of the FE directions caused by the alternating encoding polarities extending over the at least two cycles of the flow within the subject that shift the Fourier spectrum of velocity waveforms corresponding to the FE data. The method further includes using the directional FE datasets, generating an image of the subject showing flow within the subject caused by the at least two cycles of flow within the subject.

In accordance with yet another aspect of the present disclosure, a magnetic resonance imaging (MRI) system is provided. The MRI system includes a magnet system configured to generate a polarizing magnetic field about at least a portion of a subject arranged in the MRI system and a plurality of gradient coils configured to apply a gradient field to the polarizing magnetic field. The MRI system also includes a radio frequency (RF) system configured to apply an excitation field to the subject and acquire MR image data therefrom and a computer system. The computer system is programmed to control the plurality of gradient coils and the RF system to perform a phase-contrast pulse sequence to acquire imaging data. The imaging data is acquired by acquiring a first set of MR data that is flow encoded along a first direction ($FE_1$) using a two-sided flow-encoding strategy that is free of flow compensation and acquiring a second set of MR data that is flow encoded along a second direction ($FE_2$) and flow encoded along a third direction ($FE_3$) using a hybrid one- and two-sided flow encoding strategy. The computer system is further programmed to separate the first set of MR data into a background phase signal $\phi_0(t)$ and a first directional phase signal $\phi_{v,1}(t)$ and separate the second set of MR data into a second directional phase signal $\phi_{v,2}(t)$ and a third directional phase signal $\phi_{v,3}(t)$. The MRI system is also programmed to reconstruct MRA images of the subject using the background phase signal $\phi_0(t)$, the first directional phase signal $\phi_{v,1}(t)$, the second directional phase signal $\phi_{v,2}(t)$, the third directional phase signal $\phi_{v,3}(t)$.

In accordance with still another aspect of the present disclosure, a magnetic resonance imaging (MRI) system is provided. The MRI system includes a magnet system configured to generate a polarizing magnetic field about at least a portion of a subject arranged in the MRI system and a plurality of gradient coils configured to apply a gradient field to the polarizing magnetic field. The MRI system also includes a radio frequency (RF) system configured to apply an excitation field to the subject and acquire MR image data therefrom and a computer system. The computer system is programmed to control the plurality of gradient coils and RF system to acquire flow encoded (FE) data with alternating encoding polarities and along two of three orthogonal directions through the subject over at least two cycles of physiological flow within the subject. The computer system is further programmed to separate the FE data into directional FE datasets using a temporal filter that separates the FE data based on temporal modulation of the FE directions caused by the alternating encoding polarities extending over the at least two cycles of the flow within the subject that shift the Fourier spectrum of velocity waveforms corresponding to the FE data. The computer system is further programmed to use the directional FE datasets to generate an image of the subject showing flow within the subject caused by the at least two cycles of flow within the subject.

In accordance with yet another aspect of the disclosure, a method is provided for acquiring flow encoded data from a subject using a magnetic resonance imaging (MRI) system to reconstruct an image of the subject illustrating flow within the subject. The method includes (i) using the MRI system, acquiring flow encoded (FE) data with alternating encoding polarities and along at least one direction through the subject and (ii) determining a velocity of the flow within the subject in the at least one direction by analyzing a Fourier spectrum of the FE data to determine temporal modulation caused by the alternating encoding polarities that shift the Fourier spectrum. The method also includes using the FE data and the velocity of flow determined in step (ii), generating an image of the subject showing the velocity of flow within the subject.

The foregoing and other advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION

Figure 1:
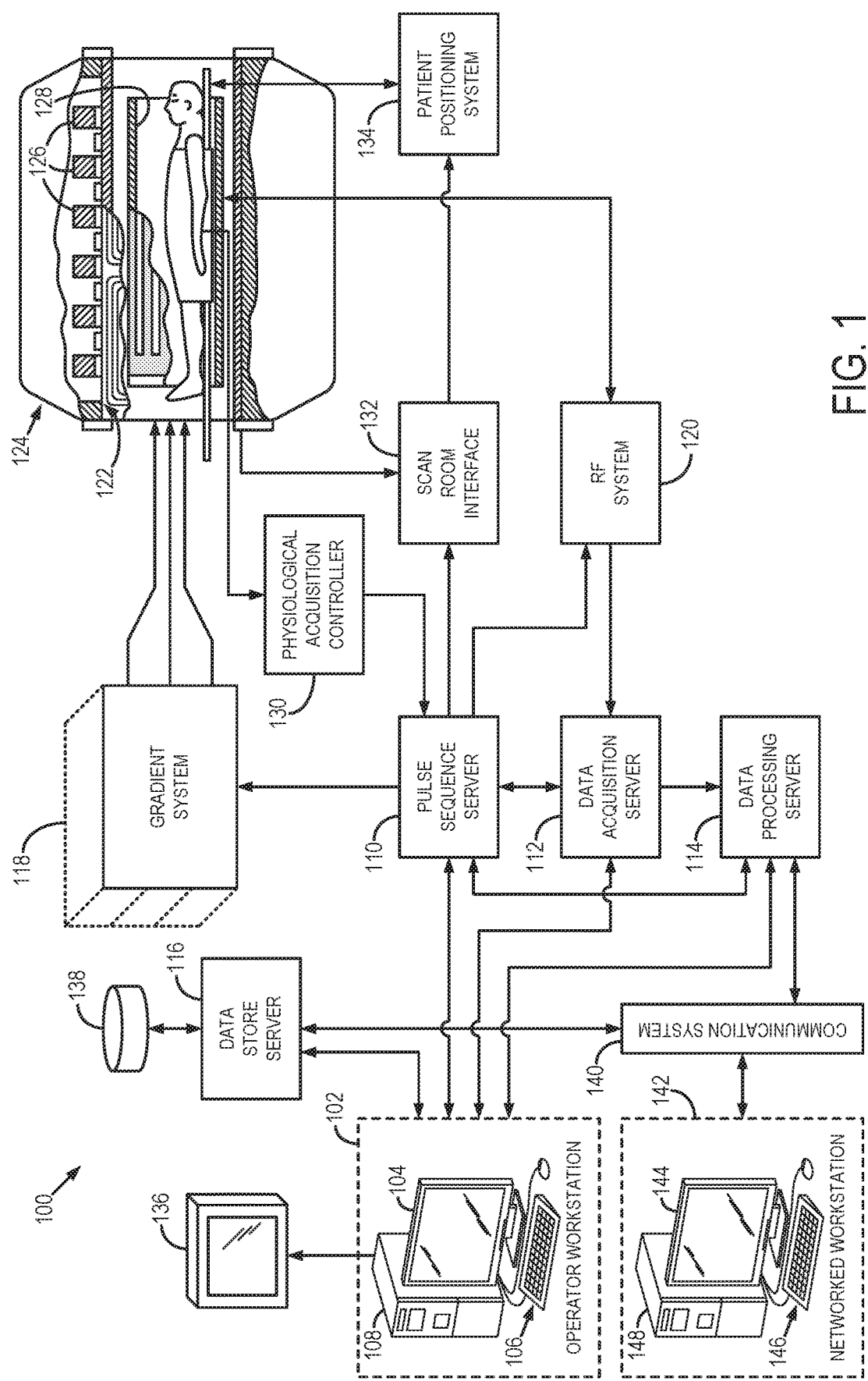
FIG. 1 is a block diagram of an MRI system for use with the present disclosure.

Referring particularly to FIG. 1, an example of a magnetic resonance imaging (MRI) system 100 is illustrated. The MRI system 100 includes a workstation 102 having a display 104 and a keyboard 106. The workstation 102 includes a processor 108 that is commercially available to run a commercially-available operating system. The workstation 102 provides the operator interface that enables scan prescriptions to be entered into the MRI system 100. The workstation 102 is coupled to four servers: a pulse sequence server 110; a data acquisition server 112; a data processing server 114; and a data store server 116. The workstation 102 and each server 110, 112, 114, and 116 are connected to communicate with each other.

The pulse sequence server 110 functions in response to instructions downloaded from the workstation 102 to operate a gradient system 118 and a radiofrequency (RF) system 120. Gradient waveforms necessary to perform the prescribed scan are produced and applied to the gradient system 118, which excites gradient coils in an assembly 122 to produce the magnetic field gradients $G_x$, $G_y$, and $G_z$ used for position encoding MR signals. The gradient coil assembly 122 forms part of a magnet assembly 124 that includes a polarizing magnet 126 and a whole-body RF coil 128 (or a head (and neck) RF coil for brain imaging).

RF excitation waveforms are applied to the RF coil 128, or a separate local coil, such as a head coil, by the RF system 120 to perform the prescribed magnetic resonance pulse sequence. Responsive MR signals detected by the RF coil 128, or a separate local coil, are received by the RF system 120, amplified, demodulated, filtered, and digitized under direction of commands produced by the pulse sequence server 110. The RF system 120 includes an RF transmitter for producing a wide variety of RF pulses used in MR pulse sequences. The RF transmitter is responsive to the scan prescription and direction from the pulse sequence server 110 to produce RF pulses of the desired frequency, phase, and pulse amplitude waveform. The generated RF pulses may be applied to the whole body RF coil 128 or to one or more local coils or coil arrays.

The RF system 120 also includes one or more RF receiver channels. Each RF receiver channel includes an RF preamplifier that amplifies the MR signal received by the coil 128 to which it is connected, and a detector that detects and digitizes the quadrature components of the received MR signal. The magnitude of the received MR signal may thus be determined at any sampled point by the square root of the sum of the squares of the I and Q components:

$$M=\sqrt{I^2+Q^2} \tag{1};$$

and the phase of the received MR signal may also be determined:

$$\varphi = \tan^{-1}\left(\frac{Q}{I}\right). \tag{2}$$

The pulse sequence server 110 also optionally receives patient data from a physiological acquisition controller 130. The controller 130 receives signals from a number of different sensors connected to the patient, such as electrocardiograph (ECG) signals from electrodes, or respiratory signals from a bellows or other respiratory monitoring device. Such signals are typically used by the pulse sequence server 110 to synchronize, or "gate," the performance of the scan with the subject's heart beat or respiration.

The pulse sequence server 110 also connects to a scan room interface circuit 132 that receives signals from various sensors associated with the condition of the patient and the magnet system. It is also through the scan room interface circuit 132 that a patient positioning system 134 receives commands to move the patient to desired positions during the scan.

The digitized MR signal samples produced by the RF system 120 are received by the data acquisition server 112. The data acquisition server 112 operates in response to instructions downloaded from the workstation 102 to receive the real-time MR data and provide buffer storage, such that no data is lost by data overrun. In some scans, the data acquisition server 112 does little more than pass the acquired MR data to the data processor server 114. However, in scans that require information derived from acquired MR data to control the further performance of the scan, the data acquisition server 112 is programmed to produce such information and convey it to the pulse sequence server 110. For example, during prescans, MR data is acquired and used to calibrate the pulse sequence performed by the pulse sequence server 110. Also, navigator signals may be acquired during a scan and used to adjust the operating parameters of the RF system 120 or the gradient system 118, or to control the view order in which k-space is sampled. In all these examples, the data acquisition server 112 acquires MR data and processes it in real-time to produce information that is used to control the scan.

The data processing server 114 receives MR data from the data acquisition server 112 and processes it in accordance with instructions downloaded from the workstation 102. Such processing may include, for example: Fourier transformation of raw k-space MR data to produce two or three-dimensional images; the application of filters to a reconstructed image; the performance of a backprojection image reconstruction of acquired MR data; the generation of functional MR images; and the calculation of motion or flow images.

Images reconstructed by the data processing server 114 are conveyed back to the workstation 102 where they are stored. Real-time images are stored in a data base memory cache (not shown), from which they may be output to operator display 112 or a display 136 that is located near the magnet assembly 124 for use by attending physicians. Batch mode images or selected real time images are stored in a host database on disc storage 138. When such images have been reconstructed and transferred to storage, the data processing server 114 notifies the data store server 116 on the workstation 102. The workstation 102 may be used by an operator to archive the images, produce films, or send the images via a network or communication system 140 to other facilities that may include other networked workstations 142.

The communications system 140 and networked workstation 142 may represent any of the variety of local and remote computer systems that may be included within a given clinical or research facility including the system 100 or other, remote location that can communicate with the system 100. In this regard, the networked workstation 142 may be functionally and capably similar or equivalent to the operator workstation 102, despite being located remotely and communicating over the communication system 140. As such, the networked workstation 142 may have a display 144 and a keyboard 146. The networked workstation 142 includes a processor 148 that is commercially available to run a commercially-available operating system. The networked workstation 142 may be able to provide the operator interface that enables scan prescriptions to be entered into the MRI system 100.

Figure 2:
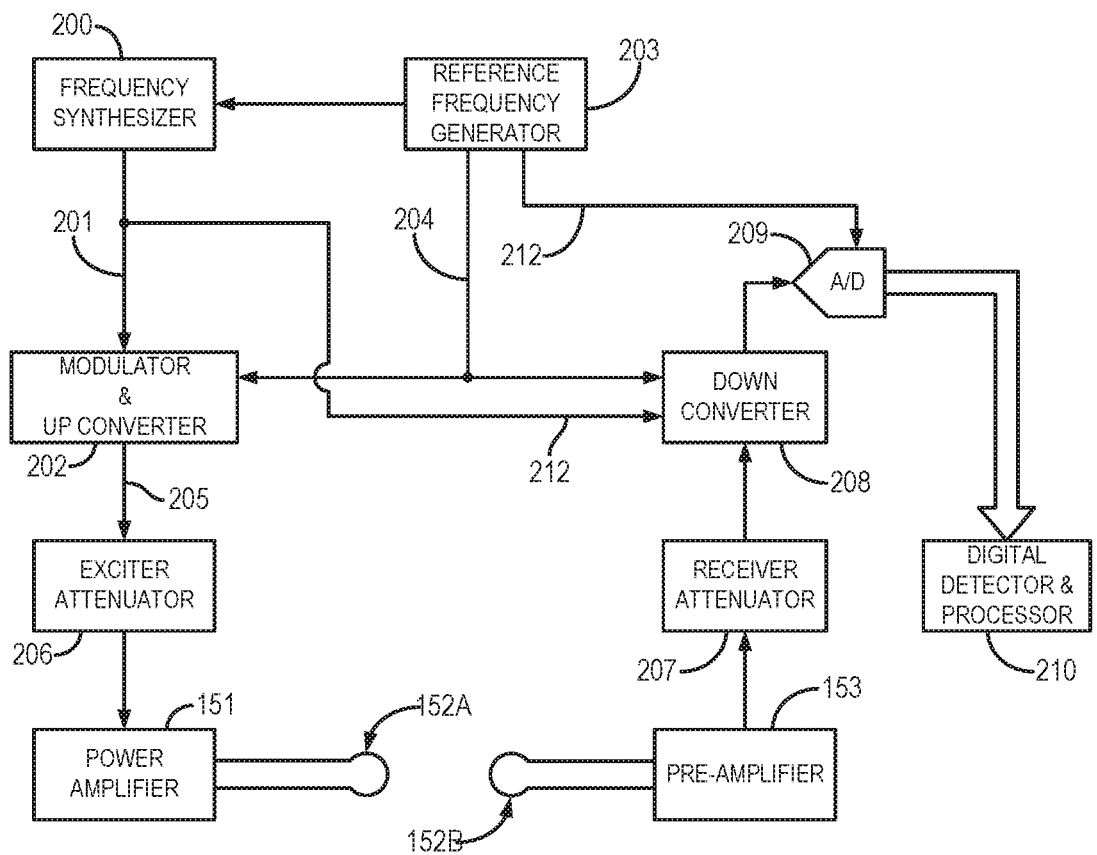
FIG. 2 is a schematic representation of a transceiver system for use with the MRI system of FIG. 1.

As shown in FIG. 1, the RF system 26 may be connected to the whole body RF coil 34, or as shown in FIG. 2, a transmitter section of the RF system 26 may connect to one RF coil 151A and its receiver section may connect to a separate RF receive coil 151B. Often, the transmitter section is connected to the whole body RF coil 34 and each receiver section is connected to a separate local coil 151B.

Referring particularly to FIG. 2, the RF system 26 includes a transmitter that produces a prescribed RF excitation field. The base, or carrier, frequency of this RF excitation field is produced under control of a frequency synthesizer 200 that receives a set of digital signals from the pulse sequence server 18. These digital signals indicate the frequency and phase of the RF carrier signal produced at an output 201. The RF carrier is applied to a modulator and up converter 202 where its amplitude is modulated in response to a signal R(t) also received from the pulse sequence server 18. The signal R(t) defines the envelope of the RF excitation pulse to be produced and is produced by sequentially reading out a series of stored digital values. These stored digital values may, be changed to enable any desired RF pulse envelope to be produced.

The magnitude of the RF excitation pulse produced at output 205 is attenuated by an exciter attenuator circuit 206 that receives a digital command from the pulse sequence server 18. The attenuated RF excitation pulses are applied to the power amplifier 151 that drives the RF coil 151A.

Referring still to FIG. 2, the signal produced by the subject is received by the receiver coil 152B and applied through a preamplifier 153 to the input of a receiver attenuator 207. The receiver attenuator 207 further amplifies the signal by an amount determined by a digital attenuation signal received from the pulse sequence server 18. The received signal is at or around the Larmor frequency, and this high frequency signal is down converted in a two-step process by a down converter 208 that first mixes the NMR signal with the carrier signal on line 201 and then mixes the resulting difference signal with a reference signal on line 204. The down converted NMR signal is applied to the input of an analog-to-digital (A/D) converter 209 that samples and digitizes the analog signal and applies it to a digital detector and signal processor 210 to produce the I values and Q values corresponding to the received signal. As described above, the resulting stream of digitized I and Q values of the received signal are output to the data acquisition server 20 of FIG. 1. The reference signal, as well as the sampling signal applied to the A/D converter 209, is produced by a reference frequency generator 203.

Figure 3A:
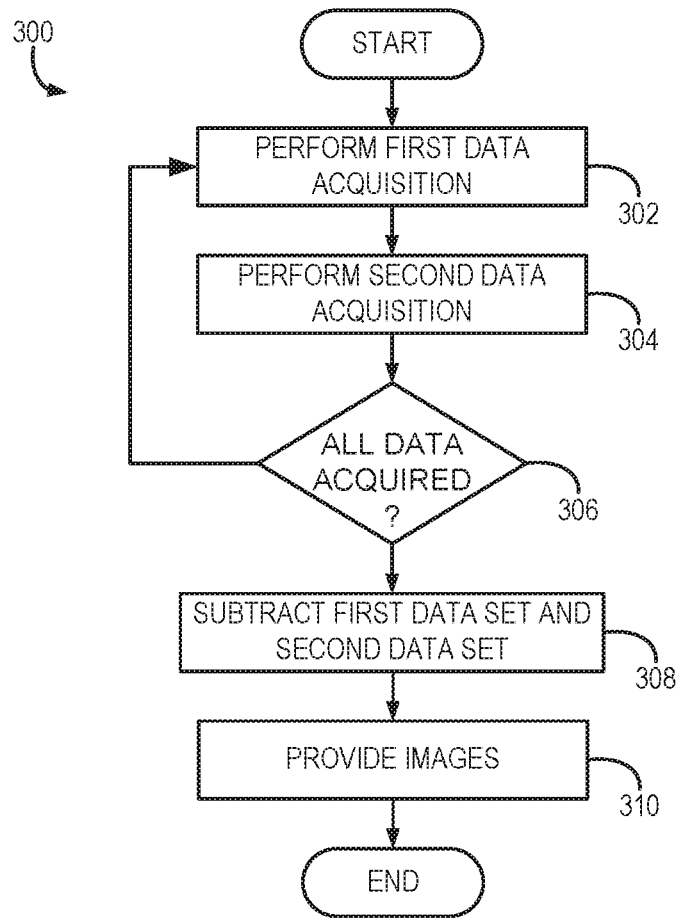
FIG. 3A is a flow chart of some examples of steps of a PC MRI imaging process.

Referring to FIG. 3A, a PC method 300 is generally performed using a first data acquisition is performed at process block 302. As illustrated in the associated pulse sequence diagram of FIG. 3B, 4D flow PCT MRI a pulse sequence is performed that, samples four waveforms within the cardiac cycle (i.e. the FC signal phase, and 3 FE signal phase waveforms in three orthogonal directions with adequate sampling frequency such that accurate 3D cardiac-phase-resolved velocity vectors for each voxel can be reconstructed by subtracting the FC waveform from each of the three FE waveforms). That is, a first acquisition is performed at process block 302, a second acquisition is performed at process block 304. These pulse sequences are repeated, until, at decision block 338, all data has been acquired. Thereafter, the data set formed from repetition of the first data acquisition at process block 302 and the data set formed from repetition of the second data acquisition at process block 304 is subtracted at process block 308. From this subtraction, at process block 310, the final images may be provided.

Figure 4:
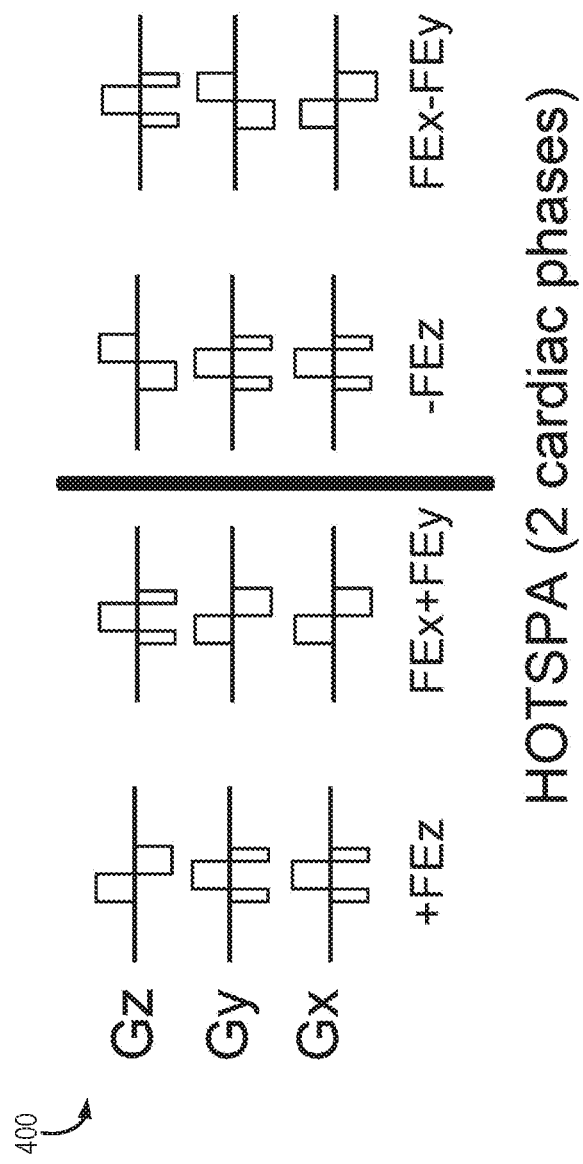
FIG. 4 is an example of one pulse sequence diagram of an imaging process in accordance with the present disclosure, showing only FC (three gradients) and ±FE gradients (bipolar gradients). For each cardiac phase, a traditional PC MRI pulse sequence requires four samples while, as illustrated in FIG. 4, the present disclosure the requisite data is acquired with two samples.

Referring to FIG. 4, and as will be further described, using a hybrid one- and two-sided FE strategy 400, a hybrid spectra (after Fourier transform in time) for each pair of the four waveforms can be efficiently encoded by modulating the temporal frequencies of these spectra.

Before turning specifically to a detailed description of particular implementations of techniques in accordance with the present disclosure, some simplified explanations will be provided, starting with a description relative to an implementation of PC MRI that relies on an FC-free, two-sided FE acquisition. Consider, for example, a conventional 2D PC-MRI acquisition, such as described above with respect to FIG. 3, that includes a single view-per-segment (VPS), where the FC and FE in the z-direction ($FE_z$) data are acquired in an interleaved fashion. In this acquisition, the data for each cardiac phase is acquired within two repetition times (TRs).

Then consider a two-sided FE strategy where only $FE_z$ data is sampled, but the polarity of the $FE_z$ M1 is alternated between successive cardiac phases. Such a 2D PC-MRI acquisition strategy is the same as the SVE technique described above. The phase for the acquired $FE_z$ signal, $\phi_z(t)$, is therefore $\phi_0(t)+\phi_{v,z}(t)$ for odd cardiac phases and $\phi_0(t)-\phi_{v,z}(t)$ for even cardiac phases, where $\phi_0(t)$ is the waveform for the FC background phase and $\phi_{v,z}(t)$ is the signal phase associated with the z component of the blood velocity. If one performs a Fourier transform of $\phi_z(t)$ in the time direction, there will be two separate spectra: the spectrum for $\phi_0(t)$ will occupy the lower frequency region, whereas the spectrum of $\phi_{v,z}(t)$ will be shifted by half of the spectral support due to the alternating 0°-180° phase modulations of the $\phi_{v,z}(t)$ waveform. The FC background phase generally does not change quickly in time; therefore, the spectrum for $\phi_0(t)$ will have narrower bandwidth compared to $\phi_{v,z}(t)$.

Figure 5:
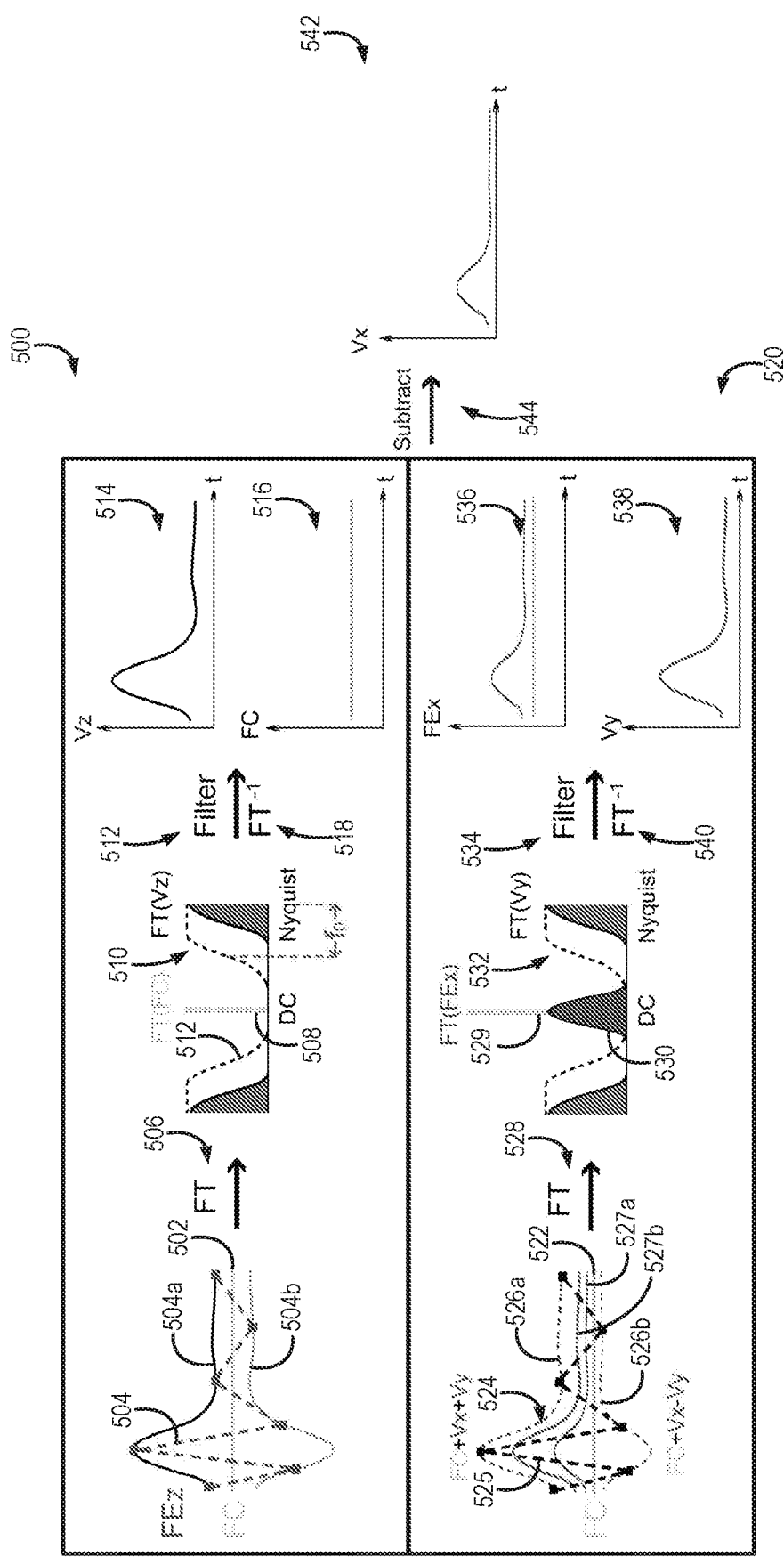
FIG. 5 is a schematic diagram of a data acquisition and processing technique in accordance with the present disclosure.

Referring to FIG. 5 this is illustrated in a first acquisition 500. In this acquisition the FC phase 502 is constant and the FC-Free Two-Sided FE ($FE_z$) alternates 504 during the cardiac cycle, which corresponds to a delta function banded by positive and negative velocity waveform 504a and 504b.

Applying a Fourier transform (506) yields a DC component corresponding to the constant FC 508 and separated FT signals 510 at Nyquist area. Due to the shifted spectrum, a filter 512 can be applied to separate the two spectra 514, 516 and recover $\phi_0(t)$ and $\phi_{v,z}(t)$ after inverse Fourier transforms 518. That is, the FT 506 of data acquired from the paired FC-free two-sided FE velocity waveform separates the velocity spectrum $FT(V_z)$ at Nyquist area and FC at low frequency region. Application of a Fermi filter (512) is applied to separate the two components.

In this scenario, due to the asymmetrical spectral support needed for the FC and $FE_z$ signals, this process approximately doubles the sampling rate for $FE_z$ and allocates the majority of the spectral bandwidth for the $\phi_{v,z}(t)$ signal and narrower bandwidth for the $\phi_0(t)$ signal. This stands in contrast to conventional 2D PC-MRI, where one is forced to assign the same spectral support for both the FC and the $FE_z$ signal. It is noted that, in this case, the temporal resolution is doubled and the temporal footprint is halved for each cardiac phase compared to conventional 2D PC-MRI (1 TR vs. 2 TR's for n VPS sampling) since no FC data is acquired.

Now a hybrid, one- and two-sided FE acquisition can be described where the HOTSPA technique is used to simultaneously acquire FE data in two orthogonal directions rather than a FC/FE pair as described above. Referring again to FIG. 5, without loss of generality, the flow velocity in the X and Y directions can be encoded using n VPS 520. In conventional PC-MRI, one would acquire the $FE_x$ and $FE_y$ signal in two successive TRs and each cardiac phase would be formed from data spanning 2 TRs. Again, the FC phase 522 is constant. However, in accordance with the present disclosure and the HOTSPA technique, both $FE_x$ and $FE_y$ are simultaneously acquired in each TR 524. More particularly, the hybrid one- and two-sided FE acquisition is shown by dash line 525, the outlines of $FC+V_x \pm V_y$ are shown in dash lines 526a and 526b, and the true flow waveforms of $V_x$ and $V_y$ are shown by lines 527a and 527b. Since velocity $V_{x/y/z}$ is proportional to the phase difference $\phi_{v,x/y/z}$, these can be treated in the above-described scheme of the HOTSPA technique as being the same. However, showing $V_{x/y/z}$ provides a more clear physics meanings than showing $\phi_{v,x/y/z}$.

The FT of data acquired using the hybrid one- and two-sided FE technique yields the spectrum of two-sided velocity encoding (i.e. $V_y$) that is separated from the DC component $FE_x(=FC+V_x)$. As shown, the flow encoding polarity is alternated between two successive cardiac phases for one direction (in this example the Y direction only), such that the signal phase $\phi_{xy}(t)$ is $\phi_0(t)+\phi_{v,x}(t)+\phi_{v,y}(t)$ for odd cardiac phases and is $\phi_0(t)+\phi_{v,x}(t)-\phi_{v,y}(t)$ for even cardiac phases. To achieve this, it is recognized that such an encoding may be conceptualized as 45 degree rotation of the FE axes; however, the sampling rate is doubled since each TR is now considered a separate cardiac phase. Similar to the above-described FC-free, two-sided FE case, a Fourier transform 528 of the $\phi_{xy}(t)$ waveform produces three distinct spectra, one for $\phi_0(t)$ 529, one for $\phi_{v,x}(t)$ 530, and one for $\phi_{v,y}(t)$ 532. The spectra of $\phi_0(t)$ 529 and $\phi_{v,x}(t)$ 530 overlap as both are at the low temporal frequency region, whereas the spectrum of $\phi_{v,y}(t)$ 532 is shifted by half the spectral support due to the alternating phase of the sampling function for the $\phi_{v,y}(t)$ signal. Again, using the shifted spectrum, a filter 534 can be applied to separate the two spectra 536, 538 and recover $\phi_0(t)$ and $\phi_{v,z}(t)$ after inverse Fourier transforms 540. For example, a Fermi filter can be applied to separate the spectra of two in-plane velocities. Thus, as illustrated in FIG. 5, from top to bottom, four separated velocity waveforms 514, 516, 536, 538 are provided after filtering and inverse Fourier transform ($FT^{-1}$). Thus, with these four waveforms, any PC weighted images can be provided.

This acquisition strategy can be extended to provide a HOTSPA 4D flow technique 542, which utilizes both the above-described FC-free, two-sided FE strategy 500 and the hybrid one- and two-sided FE strategy 520, as further illustrated in FIG. 4. Specifically, for a VPS=1 case, each cardiac phase contains data from two TRs, one for $FE_z$ using the FC-free, two-sided FE strategy 500, and one for FE in the X and Y directions, using the hybrid one- and two-sided FE strategy 520. The flow encoding polarity is alternated for the Z and Y directions during two successive cardiac phases. It is noted that the XYZ directions can be rotated to any arbitrary set of orthogonal basis in the 3D M1 space. As described, from the data acquired using the FC-free, two-sided FE strategy 500, the background phase $\phi_0(t)$ and the Z velocity $\phi_{v,z}(t)$ can be separated using a filter. The $\phi_0(t)$ spectrum can subsequently be subtracted 544 from the spectrum from the hybrid one- and two-sided FE strategy 520 and a filter can be finally applied in the resulting spectrum to separate the $\phi_{v,x}(t)$ and the $\phi_{v,y}(t)$ data. The subtraction between FC and $FE_x$ gives the velocity waveform in x-direction.

Thus, the above-described approaches can be applied to four-point balanced PC-MRI sampling (i.e., tetrahedral $M_1$ space sampling). Typical four-point balanced PC-MRI sequentially acquires: $\phi_0+\phi_x+\phi_y+\phi_z$, $\phi_0-\phi_x-\phi_y+\phi_z$, $\phi_0-\phi_x+\phi_y-\phi_z$, and $\phi_0+\phi_x-\phi_y-\phi_z$. However, the above-described systems and methods can be used to apply HOTSPA, for example, in two stages. First, four functions are defined as: $f(t)=\phi_0+\phi_y$, $f'(t)=\phi_0-\phi_y$, $g(t)=\phi_z+\phi_x$, and $g'(t)=\phi_z-\phi_x$. Hence, the four-point balanced PC-MRI samples the following flow waveforms: $f(t)+g(t)$, $f(t)-g(t)$, $f'(t)+g'(t)$, and $f'(t)-g'(t)$.

From the $f(t)+g(t)$ and $f(t)-g(t)$ data, the spectra for $f(t)$ and $g(t)$ can be separated using HOTSPA temporal filtering. From the $f'(t)+g'(t)$, and $f'(t)-g'(t)$ data, the spectra for $f'(t)$ and $g'(t)$ can be separated using HOTSPA temporal filtering. After solving for all four velocity waveforms, two additional HOTSPA temporal filterings can be applied. First, an alternating pattern of $f(t)=\phi_0+\phi_y$ and $f'(t)=\phi_0-\phi_y$ can be applied to separate the $\phi_0$ and $\phi_y$ spectra. Second, a filter for the alternating pattern of $g(t)=\phi_z+\phi_x$ and $g'(t)=\phi_z-\phi_x$ can be applied to separate the $\phi_z$ and $\phi_x$ spectra. In the four-point balanced PC-MRI case, all of the aforementioned benefits of HOTSPA apply.

In one non-limiting example, the filter may be a Fermi filter that is centered at peak of each spectrum as described by:

$$F(f) = \frac{1}{1 + \exp\left(\frac{f - f_0}{C}\right)}. \quad (3)$$

In Eqn. (3), the constant C controls the shape of the Fermi filter and C can be empirically chosen, for example, as C=0.22. Also in Eqn. (3), f represents temporal frequency, and $f_0$ is the frequency corresponding to the full-with-half-maximum (FWHM) of the Fermi filter. In this non-limiting example, $f_0$ was the frequency component with 10% of the maximum amplitude for the spectrum to be filtered or 25% of the spectral support, whichever results in a larger FWHM.

Figure 6:
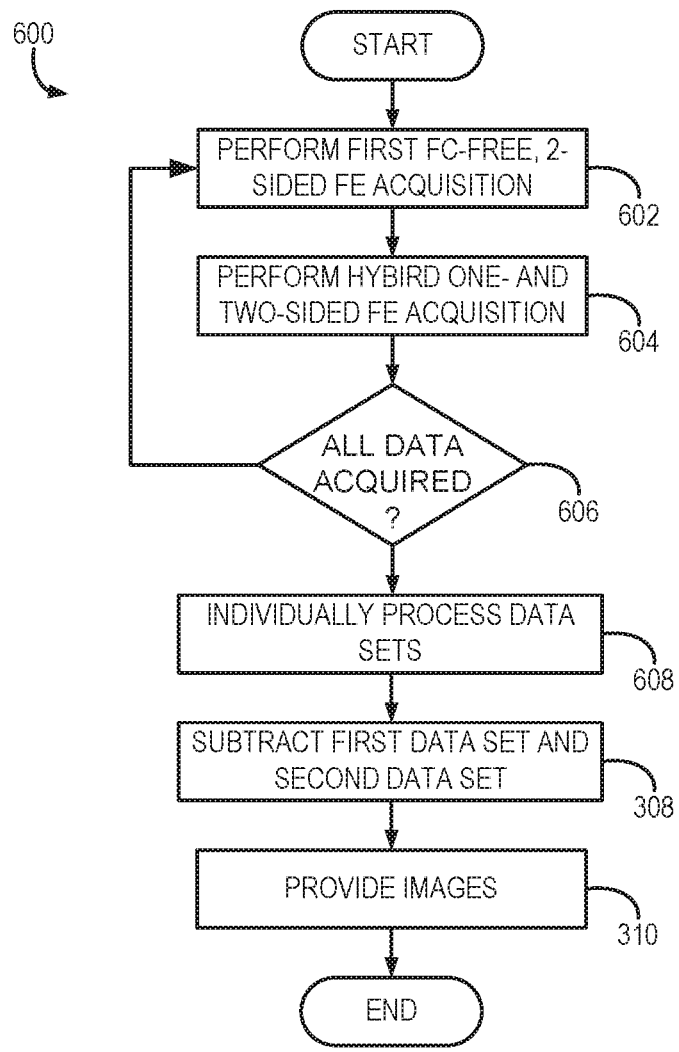
FIG. 6 is a flow chart setting forth some examples of steps of a process implementing some of the techniques described with respect to FIG. 5.
Figure 7B:
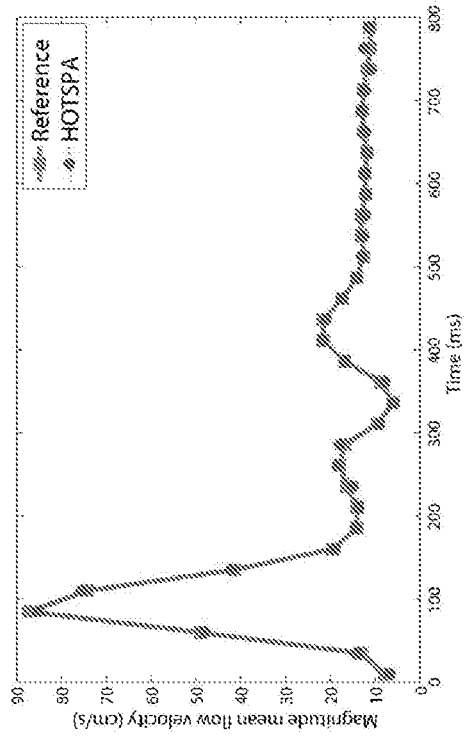
FIG. 7B is a graph showing a magnitude mean flow velocity comparison between the reference FC/3FE data and the HOTSPA data.
Figure 7D:
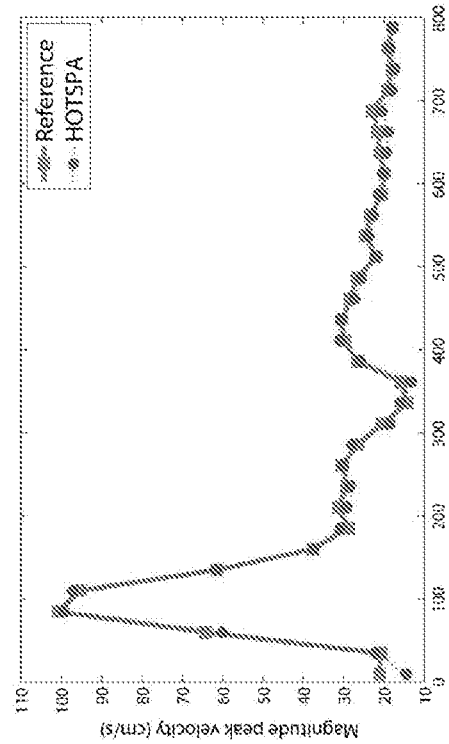
FIG. 7D is a graph showing a magnitude peak velocity comparison between the reference FC/3FE data and the HOTSPA data.
Figure 7A:
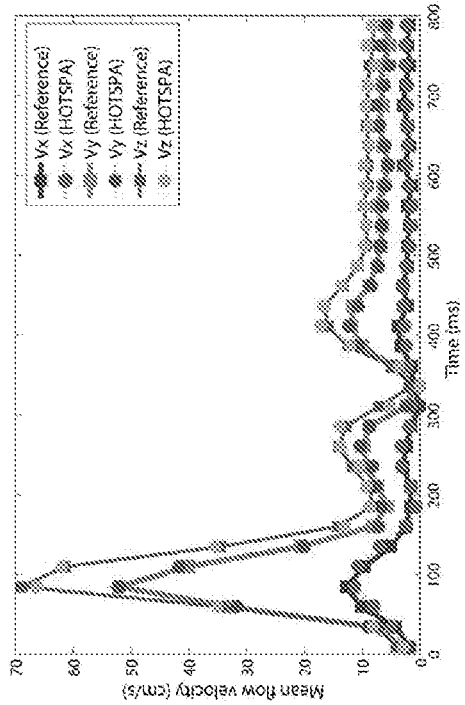
FIG. 7A is a graph showing 3D mean flow velocity comparison between reference FC/3FE data and the HOTSPA data.
Figure 7C:
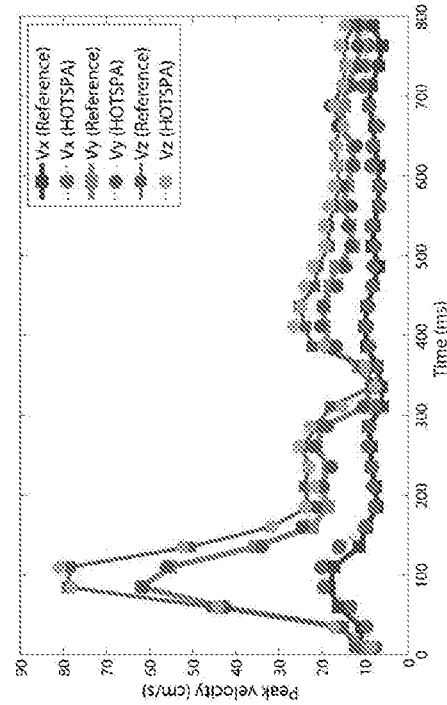
FIG. 7C is a graph showing a 3D peak velocity comparison between reference FC/3FE data and the HOTSPA data.
Figure 7F:
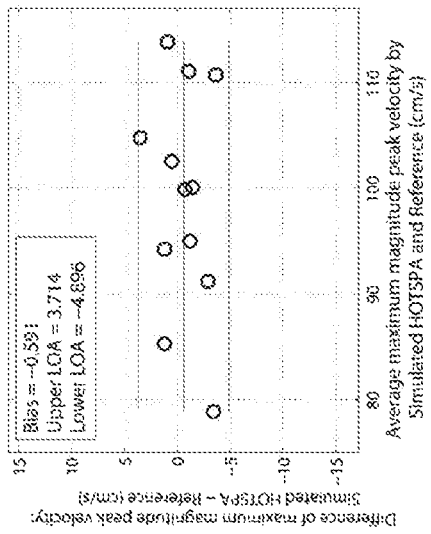
FIG. 7F is a graph showing a maximum magnitude peak velocity comparison between the reference FC/3FE data and the HOTSPA data.
Figure 7E:
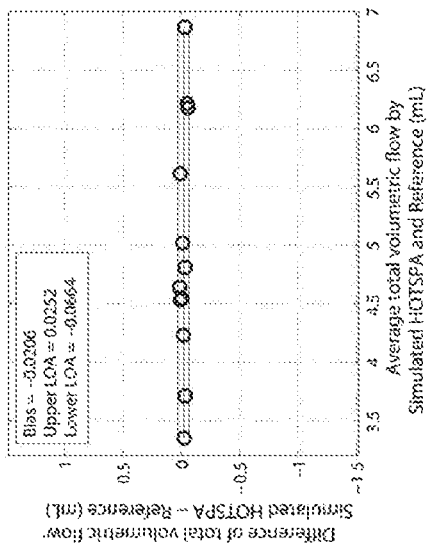
FIG. 7E is a graph showing a total volumetric flow comparison between the reference FC/3FE data and the HOTSPA data.

Referring to FIG. 6, one non-limiting example of a process implementing the above-described FC-free, two-sided FE strategy 500 and the hybrid one- and two-sided FE strategy 520 to form the HOTSPA 4D flow technique 542 is provided. Specifically, the above-described FC-free, two-sided FE strategy 500 is performed at process block 602, as is the hybrid one- and two-sided FE strategy 520 performed at process block 604 until all data is determined at decision block 606 to have been acquired.

At process block 608, the data sets are separately processed, as described with respect to FIG. 5. For example, as the HOTSPA PC-MRI reconstruction can be performed separately for each voxel, it is possible to apply Fermi filters with different pass bandwidth and/or shapes for different voxels. For example, for voxels with velocities predominately along the X direction and have negligible Y velocity, then no filter will be needed for the $\phi_{xy}(t)$ spectrum. This is because the $\phi_{v,y}(t)$ would be negligible and the entire spectral support, which is twice as wide as conventional 4D flow, and can be retrospectively allocated for $\phi_{v,x}(t)$, doubling the temporal resolution for these voxels. The same benefit is achievable for voxels with predominately Y velocity with negligible X velocity. For voxels with comparable X and Y velocity components, both in magnitude and temporal spectral bandwidth, a filter with a pass bandwidth equal to half of the spectral support can be applied to separate the $\phi_{v,x}(t)$ and $\phi_{v,y}(t)$ spectra, and in this scenario, the hybrid one- and two-sided FE data does not provide a benefit compared to conventional PC-MRI. Regardless of the flow direction, the FC-free two-sided FE data is can be acquired with a 25% gain in the overall 4D flow MRI acquisition speed compared to traditional PC MRI acquisitions.

Thereafter, at process block 610, the data sets are subtracted and, at process block 612, the desired velocity/flow encoded images, such as angiographic images, are provided or displayed.

EXAMPLE

An example study was performed on a 3T scanner with a 4-channel neck (in vivo studies) coil. As used in this study, "mean flow velocity" means the average velocity within the entire blood vessel lumen. Also, "peak velocity" means the maximum velocity within the entire blood vessel. Further, "magnitude velocity" means the square root of sum of squares of 3D velocities ($=\sqrt{V_x^2+V_y^2+V_z^2}$). The magnitude mean flow velocity can be used to indicate the average magnitude velocity within the entire blood vessel lumen, and magnitude peak velocity can be used to indicate the maximum magnitude velocity within the entire blood vessel lumen. Finally, "maximum velocity" means the maximum velocity within the entire cardiac cycle. This often happens in the peak systolic cardiac phases.

Retrospective In Vivo Study (2D)

The commons carotid arteries (CCAs) of six volunteers were scanned using a 2D PC-MRI sequence with 3 FE directions (FC/3FE). The sequence parameters included: VENC=100-110 cm/s, flip angle=20°, readout bandwidth=500 Hz/Pixel, TE=3.92 ms, TR=6.28 ms, Views-per-segment=1, acquired matrix=256×176, FOV=200×176 mm$^2$, and slice thickness=7 mm. The imaging plane of each data set was at approximate 50° (instead of 90°) angle to the longitudinal axis of the CCAs so that the flow velocity has significant components in more than one direction. All scans were acquired during free breathing with prospective ECG gating and the 3D flow velocity waveforms were calculated for each pixel using conventional phase-contrast MRI reconstruction. Based on these ground truth velocity waveforms, we simulated a HOTSPA dataset and calculated what $\phi_z(t)$ and $\phi_{xy}(t)$ would have been for each cardiac phase if the HOTSPA acquisition strategy was employed. The quantitative flow and velocities calculated based on the simulated HOTSPA dataset were subsequently compared with the reference 2D FC/3FE PC-MRI results.

To demonstrate the benefits of HOTSPA over the previously-described SVE technique, one volunteer's two-sided z-directional FE data was used to independently perform the HOTSPA and the SVE velocity calculation, and the maximum peak velocity measurement accuracy of HOTSPA and SVE was compared at two different temporal resolutions (25.12 ms by using all cardiac phase of the simulated two-sided FEz data and 50.24 ms using only odd cardiac phases of the two-sided FE$_z$ data).

Prospective In Vivo Study

The HOTSPA acquisition strategy was implemented for a 3T MRI system. Six volunteers were scanned at the CCAs using the 2D FC/3FE PC-MRI sequence and our prospective 2D HOTSPA sequence. Both sequences were implemented with: VENC=100-110 cm/s, flip angle=20°, readout bandwidth=500 Hz/Pixel, TE=3.92 ms, TR=6.28 ms, VPS=1 and 2 for FC/3FE, and 2 only for HOTSPA, acquired matrix=256×176, FOV=200×176 mm$^2$, and slice thickness=7 mm. Imaging plane of each data set was at approximate 50° angle to the longitudinal axis of the CCAs.

After the 2D study, six additional adult volunteers were scanned at the CCAs using the conventional 4D flow sequence and our 4D HOTSPA sequence with the following parameters: VENC=100-110 cm/s, flip angle=20°, readout bandwidth=815 Hz/Pixel, TE=3.61-3.90 ms, TR=6.13-6.42 ms, Views-per-segment=4 for conventional 4D flow and HOTSPA, acquired matrix=256×176×8, FOV=200×176×20 mm$^2$. All 2D/4D in vivo scans in this study were acquired during free breathing with prospective ECG gating. For each data set, three slices (slice 2, 4, 6 along z-direction) were selected to compare total volumetric flow measurements and maximum magnitude peak velocity measurements.

Results

Retrospective In Vivo Study

Figure 3B:
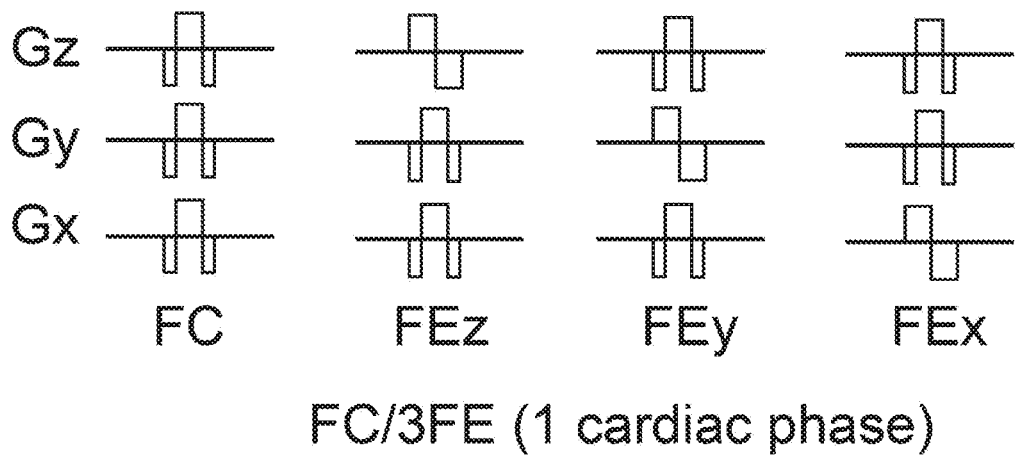
FIG. 3B is an example of one flow contrast pulse sequence that extends over one cardiac phase.

Referring to FIG. 3A, a comparison of 3D mean flow velocities is provided against reference FC/3FE and the simulated HOTSPA data. In FIG. 3B the magnitude mean flow velocity is shown for this study. The directional and magnitude mean flow velocities within region of interest (ROI) though cardiac cycle show excellent agreement between the reference FC/3FE and the simulated HOTSPA. The average root mean squared error (RMSE) of mean flow velocities of all six volunteer's CCAs were: 1.06 (range: 0.75-1.31) cm/s for z-direction, 0.91 (range: 0.73-1.52) cm/s for y-direction, 0.80 (range: 0.41-1.17) cm/s for x-direction, and 1.16 (range: 0.73-1.72) cm/s for magnitude.

Also, FIG. 3C shows a comparison of 3D peak velocities between the reference FC/3FE and the simulated HOTSPA and FIG. 3D shows a comparison of magnitude peak velocity between the two techniques. The peak velocity waveforms also showed good agreement between the reference 2D FC/3FE and the simulated HOTSPA data. The average RMSE of peak velocities of all six volunteer's CCAs were: 1.69 (range: 1.33-2.12) cm/s for z-direction, 1.60 (range: 1.28-2.30) cm/s for y-direction, 1.70 (range: 1.25-2.12) cm/s for x-direction, and 2.13 (range: 1.52-3.00) cm/s for magnitude.

Bland-Altman plots of total volumetric flow and maximum magnitude peak velocity measurements among the 6 volunteers between the two techniques are shown in FIGS. 3E and 3F. The bias of total volumetric flow was −0.02 mL (−0.4% relative bias error) with 95% confidential interval (CI) [−0.07, 0.03] mL. The bias of maximum magnitude peak velocity was −0.59 cm/s (−0.6% relative bias error) with 95% CI [−4.9, 3.7] cm/s. The Bland-Altman plots show that the total volumetric flow and maximum magnitude peak velocity measurements of HOTSPA and FC/3FE had good agreement.

Thus, FIGS. 7A-7F demonstrate that the above-described HOTSPA 4D flow technique, as well as the components of the HOTSPA 4D flow technique (i.e., FC-free, two-sided FE strategy and the hybrid one- and two-sided FE strategy) provide substantial advantages over traditional PC MRI techniques. Namely, the study demonstrates the ability to deliver reduced temporal resolution and temporal footprint compared to traditional PC MRI techniques, with particular gains in the context of 4D flow acquisitions.

Figure 8A:
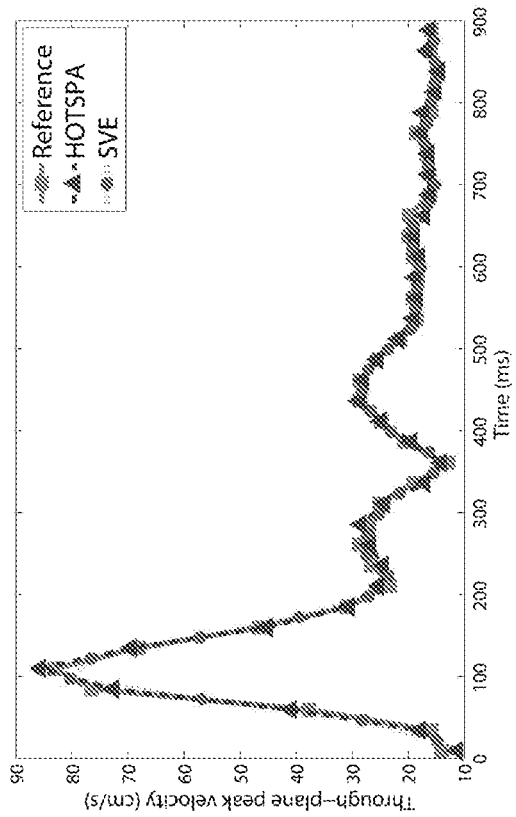
FIG. 8A is a graph showing an example of comparisons of z-directional peak velocity waveforms reconstructed by simulated HOTSPA and SVE with different temporal resolution when the temporal resolution is 25 ms.
Figure 8B:
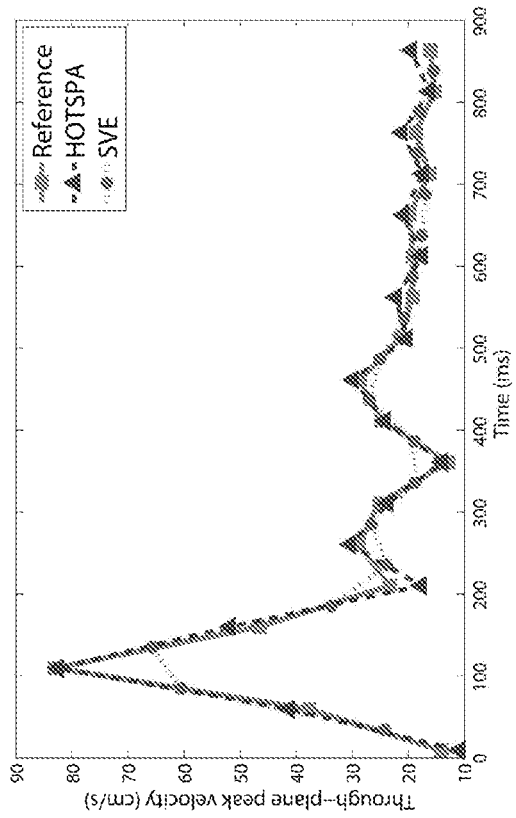
FIG. 8B is a graph showing an example of comparisons of z-directional peak velocity waveforms reconstructed by simulated HOTSPA and SVE with different temporal resolution when the temporal resolution is 50 ms.

For example, FIGS. 8A and 8B provide a comparison between HOTSPA and SVE peak velocity waveforms based on the same data from the simulated HOTSPA acquisition. At 25.12 ms temporal resolution described above with respect to FIG. 7A, both HOTSPA and SVE could provide accurate maximum peak velocity measurements compared to the reference. When the FE$_z$ data was decimated to 50.24 ms temporal resolution as described above with respect to FIG. 7B, the HOTSPA was able to provide accurate maximum peak velocity measurement with <1% relative error compared to the reference (82.5 cm/s for HOTSPA vs. 83 cm/s for the reference), while the SVE results under-estimated the maximum peak velocity by 21% (65.7 cm/s vs. 83 cm/s).

Prospective In Vivo Study

Figure 9B:
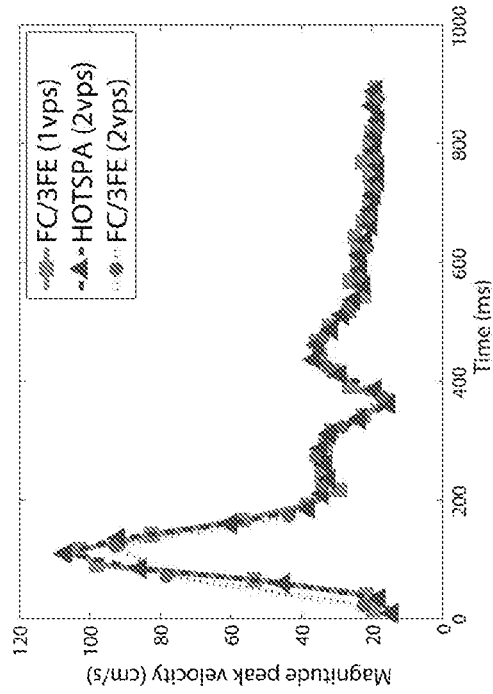
FIG. 9B is a graph showing magnitude peak velocity waveforms comparing the techniques of the present disclosure to traditional PC MRI techniques.
Figure 9D:
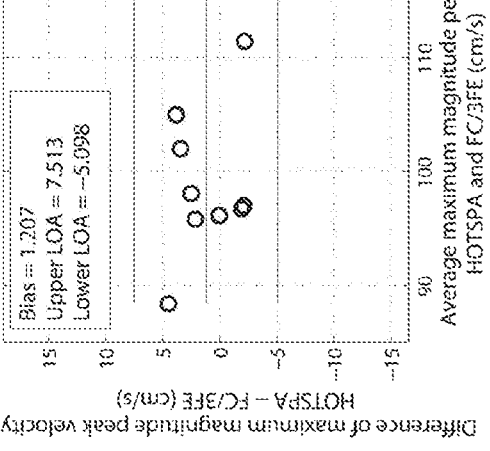
FIG. 9D is a graph showing Bland-Altman plot of maximum magnitude peak velocity measurements comparing the techniques of the present disclosure to traditional PC MRI techniques.
Figure 9A:
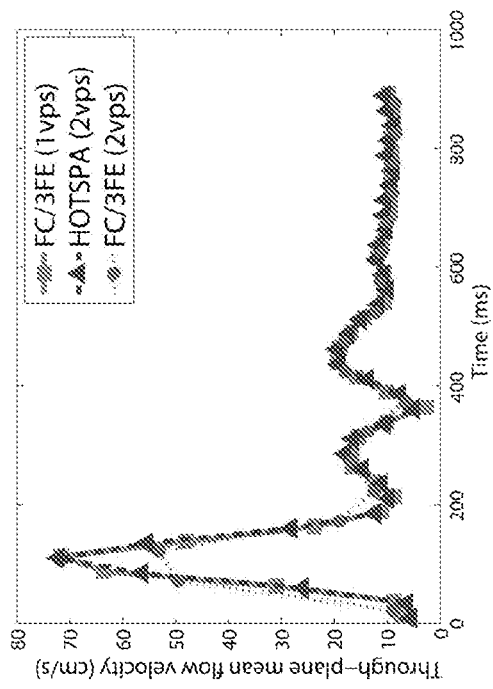
FIG. 9A is a graph showing through-plane mean flow velocity waveforms comparing the techniques of the present disclosure to traditional PC MRI techniques.
Figure 9C:
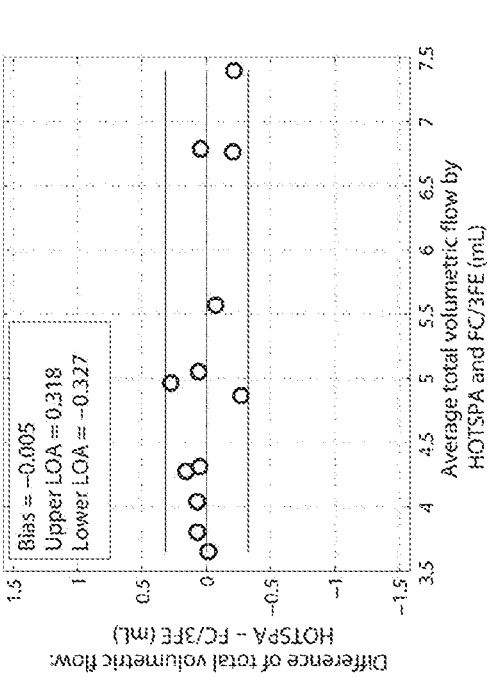
FIG. 9C is a graph showing Bland-Altman plot of total volumetric flow measurements comparing the techniques of the present disclosure to traditional PC MRI techniques.

As shown in FIGS. 9A through 9D, an example of through-plane mean flow velocity waveform and magnitude peak velocity waveform within the ROI is provided comparing three different measurements: 1) the standard 2D FC/3FE with 1 VPS and 25.12 ms temporal resolution; 2) the prospective HOTSPA with 2 VPS and 25.12 ms temporal resolution; 3) the standard 2D FC/3FE with 2 VPS and 50.24 ms temporal resolution. The mean through-plane flow velocity is illustrated in FIG. 9A and the magnitude peak velocity waveforms based on the HOTSPA acquisition with 2 VPS were similar to the 2D FC/3FE with 1 VPS is shown in FIG. 9B, although the HOTSPA total acquisition time was 50% of the 1 VPS 2D FC/3FE. However, the 2 VPS 2D FC/3FE underestimated the maximum peak velocity, presumably due to its long temporal footprint and low temporal resolution. The Bland-Altman plot of total volumetric flow within the cardiac cycle measured in the six volunteers using HOTSPA and 1-VPS FC/3FE PC-MRI is shown in FIG. 9C. Using the 1 VPS FC/3FE as the reference, the bias for HOTSPA was −0.005 mL (−0.1% relative bias error) and the 95% CI was [−0.33, 0.32] mL. The Bland-Altman plot of maximum magnitude peak velocity of FIG. 9D shows that the bias was 1.207 cm/s (1.14% relative bias error) and the 95% CI was [−5.10, 7.51] cm/s. The maximum magnitude peak velocities of all 12 CCAs measurements from HOTSPA (average=105.7 cm/s, range: 90.6-130.2 cm/s) and 1 VPS 2D FC/3FE (average=104.5 cm/s, range: 86.1-123.8 cm/s) were significantly higher than the 2 VPS 2D FC/3FE measurements (average=90.6 cm/s, range: 76.7-112.4 cm/s) ($P<0.05$, one-side paired t-test).

Figure 10A:
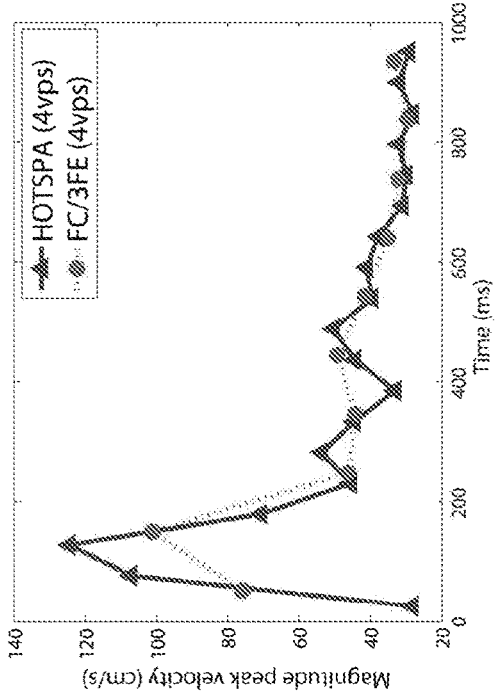
FIG. 10A is a graph showing through-plane mean flow velocity waveforms and magnitude peak velocity waveforms.
Figure 10B:
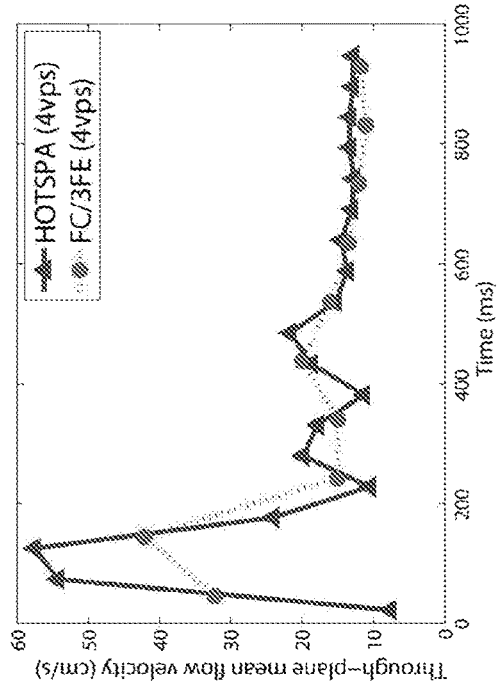
FIG. 10B is a graph showing through-plane mean flow velocity waveforms of one selected slice from the 4 VPS FC/3FE with 98.08 ms temporal resolution, and HOTSPA with 51.36 ms temporal resolution.
Figure 10C:
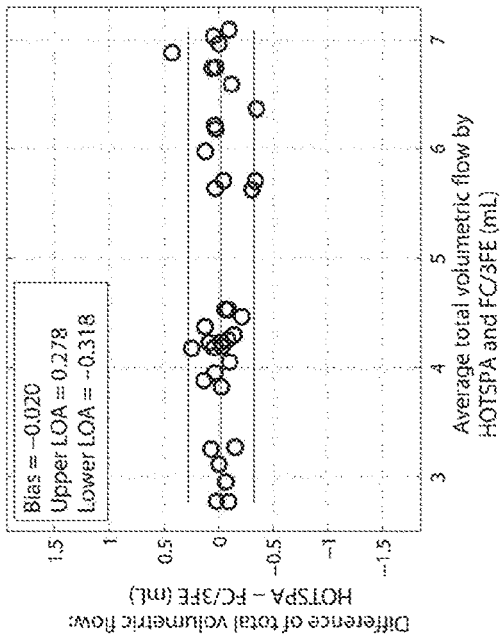
FIG. 10C is a graph showing Bland-Altman plots of total volumetric flow measurements based on data acquired using 4D FC/3FE and 4D HOTSPA.

Finally, FIGS. 10A and 10B show an example of through-plane mean flow velocity and magnitude peak velocity within the ROI in one slice of 4D flow data comparing two different measurements: 1) the standard 4D FC/3FE with 4 VPS and 98.08 ms temporal resolution; 2) the HOTSPA technique with 4 VPS and 51.36 ms temporal resolution. The HOTSPA showed higher maximum magnitude peak velocity compared with FC/3FE due to the shorter temporal footprint and higher temporal resolution. As shown in FIG. 10C, the bias of Bland-Altman of total volumetric flow measurements was −0.02 mL (−0.40% relative bias error compared to 4D FC/3FE) and the 95% CI was [−0.32, 0.28] mL. The maximum magnitude peak velocities from 4 VPS HOTSPA (average=98.0 cm/s, range: 73.7-125.6 cm/s) was significantly higher than the 4 VPS FC/3FE (average=83.2 cm/s, range: 60.2-109.6 cm/s) ($P<0.05$, one-sided paired t-test). On average, the 4 VPS FC/3FE underestimated the maximum magnitude peak velocity by 18% when compared with the 4 VPS HOTSPA.

Discussion

Thus, a flexible flow encoding strategy is provided for 4D flow MRI with improved temporal resolution and temporal footprint using temporal modulation of the flow encoding waveforms. In the HOTSPA technique, the four acquisitions (FC and 3 FE directions) of conventional FC/3FE have been reduced to two acquisitions with alternating encoding polarities for two of the three orthogonal FE directions (e.g. Z & Y directions) between two successive cardiac phases. This is clinically feasible because the temporal modulation of the FE directions shifts the Fourier spectrum of the velocity waveform for the direction with alternating polarity, which enables separation of the spectra for all three FE directions using a temporal filter. The conventional PC-MRI flow calculation is typically performed separately for each cardiac phase and recent k-t acceleration methods focus on performing a temporal modulation of sampling pattern in an under-sampled k-space. The HOTSPA technique provided herein provides a temporal modulation strategy for an under-sampled M1 space. Compared to conventional PC-MRI, HOTSPA enables a 50% shorter temporal footprint for each cardiac phase, which translates to more accurate peak flow velocity measurements while maintaining the measurement accuracy of total volumetric flow. Also, HOTSPA allows more flexible temporal filter spectral bandwidth on a voxel-by-voxel basis, whereas conventional PC-MRI effectively forces each FE direction to use the same spectral bandwidth, regardless whether or not there is significant flow in that FE direction for a given voxel. Furthermore, the temporal filter bandwidth for each FE direction can be retrospectively determined using HOTSPA for a given voxel, based on the actual acquired composite spectra for that voxel. It should be noted that HOTSPA can be combined with other k-space acceleration methods, such as parallel imaging and compressed sensing, to further accelerate data acquisition. Other techniques may include non-Cartesian sampling trajectories or sequence gradient optimization techniques that may be used with the above-described systems and methods.

HOTSPA technique provides more flexible choices of temporal resolution selections. The temporal resolution and footprint of HOTSPA can be controlled, for example, to be equal to 2*TR*views-per-segment, while the conventional FC/3FE equals to 4*TR*views-per-segment. For example, 2D PC-MRI experiments show that the HOTSPA technique can provide 12.5, 25, 37.5, 50 ms temporal resolution and temporal footprint selection; however, conventional FC/3FE can only provide 25, 50 ms. With this in mind, an application that needs 40 ms temporal resolution requires one to choose 1 VPS with 25 ms temporal resolution to maintain the measurement accuracy when using conventional FC/3FE. On the other hand, the HOTSPA technique enables the use of 3 VPS with 37.5 ms temporal resolution.

The present invention has been described in terms of one or more preferred embodiments, and it should be appreciated that many equivalents, alternatives, variations, and modifications, aside from those expressly stated, are possible and within the scope of the invention.

The invention claimed is:
1. A method for producing magnetic resonance flow images of a subject, the method including steps comprising:
  performing, using a magnetic resonance imaging (MRI) system, a phase-contrast pulse sequence to acquire imaging data by:
    acquiring a first set of MR data that is flow encoded along a first direction ($FE_1$) using a two-sided flow-encoding strategy that is free of flow compensation;
    acquiring a second set of MR data that is flow encoded along a second direction ($FE_2$) and flow encoded along a third direction ($FE_3$) using a hybrid one- and two-sided flow encoding strategy;
    separating the first set of MR data into a background phase signal $\phi_0(t)$ and a first directional phase signal $\phi_{v,1}(t)$;
    separating the second set of MR data into a second directional phase signal $\phi_{v,2}(t)$ and a third directional phase signal $\phi_{v,3}(t)$; and
    reconstructing flow images of the subject using the background phase signal $\phi_0(t)$, the first directional phase signal $\phi_{v,1}(t)$, the second directional phase signal $\phi_{v,2}(t)$, and the third directional phase signal $\phi_{v,3}(t)$.

2. The method of claim 1 wherein acquiring the second set of MR data is performed over at least two cardiac cycles of the subject using flow encoding polarity that is alternated between successive cardiac phases for the third direction and is not alternated between successive cardiac phases for the second direction.

3. The method of claim 1 wherein separating the first set MR data or separating the second set of MR data includes using a temporal filter to separate temporal spectra of a blood velocity waveform derived from the first set of MR data or the second set of MR data.

4. The method of claim 1 wherein the flow images are 3D velocity encoded images of the subject.

5. A magnetic resonance imaging (MRI) system comprising:
- a magnet system configured to generate a polarizing magnetic field about at least a portion of a subject arranged in the MRI system;
- a plurality of gradient coils configured to apply a gradient field to the polarizing magnetic field;
- a radio frequency (RF) system configured to apply an excitation field to the subject and acquire MR image data therefrom;
- a computer system programmed to:
- control the plurality of gradient coils and the RF system to perform a phase-contrast pulse sequence to acquire imaging data by:
  - acquiring a first set of MR data that is flow encoded along a first direction ($FE_1$) using a two-sided flow-encoding strategy that is free of flow compensation;
  - acquiring a second set of MR data that is flow encoded along a second direction ($FE_2$) and flow encoded along a third direction ($FE_3$) using a hybrid one- and two-sided flow encoding strategy;
- separate the first set of MR data into a background phase signal $\phi_0(t)$ and a first directional phase signal $\phi_{v,1}(t)$;
- separate the second set of MR data into a second directional phase signal $\phi_{v,2}(t)$ and a third directional phase signal $\phi_{v,3}(t)$; and
- reconstruct magnetic resonance angiography (MRA) images of the subject using the background phase signal $\phi_0(t)$, the first directional phase signal $\phi_{v,1}(t)$, the second directional phase signal $\phi_{v,2}(t)$, and the third directional phase signal $\phi_{v,3}(t)$.

6. The system of claim 5 wherein the computer system is further programmed to acquire the second set of MR data over at least two cardiac cycles of the subject using flow encoding polarity that is alternated between successive cardiac phases for the second direction and the third direction.

7. The system of claim 5 wherein the computer system is further programmed to separate the first set MR data or separate the second set of MR data includes using a temporal filter to separate temporal spectra of a blood velocity waveform derived from the first set of MR data or the second set of MR data.

* * * * *